United States Patent
Clarke et al.

(10) Patent No.: US 9,506,841 B2
(45) Date of Patent: Nov. 29, 2016

(54) TISSUE SLICER SYSTEM HAVING A TISSUE SLICING MOLD FOR RAPID GROSSING AND HYPERSAMPLING OF LARGE SURGICAL SPECIMENS

(71) Applicants: Gina Clarke, Toronto (CA); Jonathan Ho, Toronto (CA); Gordon E. Mawdsley, Toronto (CA); David R. Green, Toronto (CA); Martin Yaffe, Toronto (CA)

(72) Inventors: Gina Clarke, Toronto (CA); Jonathan Ho, Toronto (CA); Gordon E. Mawdsley, Toronto (CA); David R. Green, Toronto (CA); Martin Yaffe, Toronto (CA)

(73) Assignee: Sunnybrook Research Institute, Ontario (CA)

( * ) Notice: Subject to any disclaimer, the term of this patent is extended or adjusted under 35 U.S.C. 154(b) by 0 days.

(21) Appl. No.: 14/625,582

(22) Filed: Feb. 18, 2015

(65) Prior Publication Data

US 2015/0233799 A1    Aug. 20, 2015

Related U.S. Application Data

(60) Provisional application No. 61/942,145, filed on Feb. 20, 2014.

(51) Int. Cl.
*A61B 10/00* (2006.01)
*G01N 1/06* (2006.01)

(52) U.S. Cl.
CPC .......... *G01N 1/06* (2013.01); *G01N 2001/061* (2013.01)

(58) Field of Classification Search
CPC ....................................................... G01N 1/06
See application file for complete search history.

(56) References Cited

U.S. PATENT DOCUMENTS

| | | | | |
|---|---|---|---|---|
| 1,202,158 A | * | 10/1916 | Caldwell et al. | B26D 1/547 83/437.2 |
| 3,564,961 A | * | 2/1971 | Burkhardt | G01N 1/06 83/412 |
| 4,249,445 A | * | 2/1981 | Browning | B26B 29/063 83/454 |
| 5,383,384 A | * | 1/1995 | Dennis | B26B 29/063 83/446 |

* cited by examiner

*Primary Examiner* — Jyoti Nagpaul
(74) *Attorney, Agent, or Firm* — Quarles & Brady, LLP

(57) ABSTRACT

A tissue slicer system that includes a tissue slicing mold capable of producing very thin (e.g., on the order of 3 mm) and uniform slices to be captured from whole, fresh tissue specimens, notably breast lumpectomies, while minimizing distortion. These thin, uniform whole-specimen slices of the fresh surgical specimen increase the area of tissue available for inspection, reduce the amount of tissue lost in trimming during microtomy, and permit tissue processing for producing whole-mount sections.

16 Claims, 1 Drawing Sheet

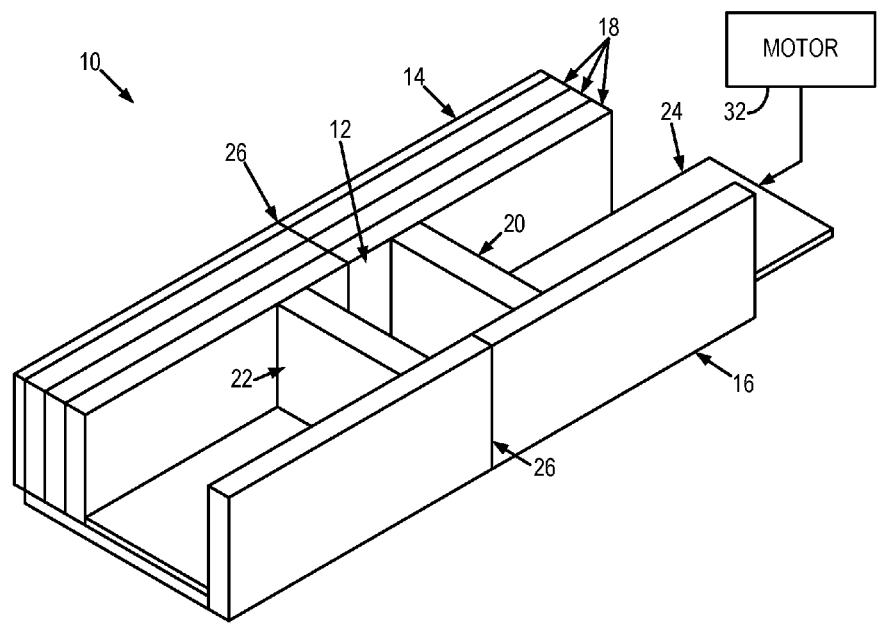
FIG. 1
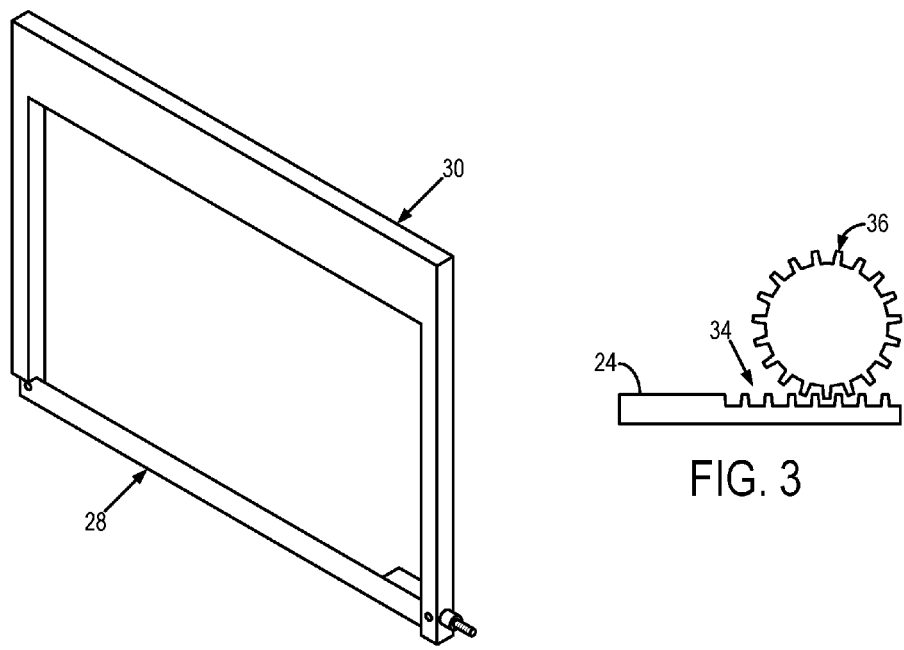
FIG. 2
FIG. 3

TISSUE SLICER SYSTEM HAVING A TISSUE SLICING MOLD FOR RAPID GROSSING AND HYPERSAMPLING OF LARGE SURGICAL SPECIMENS

CROSS-REFERENCE TO RELATED APPLICATIONS

This application claims the benefit of U.S. Provisional Patent Application Ser. No. 61/942,145, filed on Feb. 20, 2014, and entitled "TISSUE SLICER SYSTEM HAVING A TISSUE SLICING MOLD FOR RAPID GROSSING AND HYPERSAMPLING OF LARGE SURGICAL SPECIMENS."

BACKGROUND OF THE INVENTION

The field of the invention is systems and methods for grossing tissue and preparing a tissue for pathology processing, such as histology, histochemistry, and the like. More particularly, the invention relates to systems and methods for rapid grossing and hypersampling of large surgical specimens.

In routine clinical work, surgical specimens are prepared for pathology processing by gross serial slicing. This serial slicing is usually performed free-hand. Under such conditions, especially for fatty tissues that lack internal support (e.g., breast tissue), the specimen becomes distorted and the minimum achievable slice thickness is limited to approximately 10 millimeters. The significant thickness of these tissue slices limits the ability to perceive diseased regions that lie deeper within the tissue slices. As a result of this limitation, the accuracy of tissue sampling in pathology is generally reduced for such tissue slices, resulting in a missed diagnosis of disease. The thickness of the tissue slices also increases the time needed for fixation, which may violate the guidelines for processing that tissue.

Although few devices are available for standardized gross slicing of hard specimens, these technologies are inadequate for flaccid specimens such as breast which require additional support.

SUMMARY OF THE INVENTION

The present invention overcomes the aforementioned drawbacks by providing a system and method for rapid grossing and hypersampling of large surgical specimens that is capable of obtaining tissue slices thinner than 10 mm.

It is an aspect of the invention to provide a tissue slicer system for slicing a biological tissue specimen into a plurality of substantially uniformly thick slices. The tissue slicer system includes a tissue slicing mold configured to receive a biological tissue specimen and a sliding stage coupled to the tissue slicing mold. The tissue slicing mold includes a first plate, a second plate opposing the first plate, a first cross plate removably positioned between and generally perpendicular to the first plate and the second plate, and a second cross plate opposing the first cross plate and removably positioned between and generally perpendicular to the first plate and the second plate. The tissue slicing mold also includes a slit disposed in the first plate and the second plate, the slit defining a guide for a blade. The is configured to be slidably adjustable relative to the slit so as to align the tissue slicing mold with a plurality of different slicing planes.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1 illustrates an example of a tissue slicer system that is capable of providing very thin and uniform slices of a biological tissue specimen; and FIG. 2 illustrates an example of a blade and blade holder than can be used with the tissue slicer system of FIG. 1.

FIG. 3 illustrates an example rack and pinion mechanism on a sliding stage of a tissue slicer system.

DETAILED DESCRIPTION OF THE INVENTION

Described here is a tissue slicer system capable of producing very thin (e.g., on the order of 3 mm) and uniform slices to be captured from whole, fresh tissue specimens while minimizing distortion. As an example, the fresh tissue specimens can be breast lumpectomies. As other examples, however, the tissue specimens can be from other tissue types, including prostate, colon, liver, brain, and so on. These thin, uniform whole-specimen slices of the fresh surgical specimen increase the area of tissue available for inspection, reduce the amount of tissue lost in trimming during microtomy, and permit tissue processing for producing whole-mount sections.

For tissue specimens such as breast tissue, the design of the tissue slicing system makes it possible for the gross serial slicing and consequent immersion in fixative to be completed within the one-hour guideline for cold ischemic time for breast tissues. This guideline has been established to minimize autolysis and ensure stability of prognostic receptors for testing and therefore accurate planning of any secondary treatments. Similar benefits can be achieved for other tissue types.

A tissue slicer system 10 provides an adjustable tissue slicing mold 12 for receiving a supportive hydrogel suitable for encapsulating a surgical specimen for slicing. The adjustable dimensions of the tissue slicing mold 12 reduce excess hydrogel to the minimum amount that is required to support thin slicing. As a result, this adjustability of the tissue slicer system 10 reduces the associated cooling time.

The tissue slicer system 10 includes a first plate 14 opposing a second plate 16. The internal width of the tissue slicer system 10, and thus the width of the tissue slicing mold 12, is defined by the size of the space between the first and second plates 14, 16 and can be adjusted by inserting one or more spacers 18 between the first and second plates 14, 16. Preferably, the first and second plates 14, 16 and the one or more spacers 18, are all parallel to each other.

The tissue slicer system 10 also includes a removable first cross plate 20 opposing a removable second cross plate 22. The first and second cross plates 20, 22 can be removably positioned between the first and second plates 14, 16. The size of the first and second cross plates 20, 22 is determined by the effective internal width of the tissue slicer system 10; thus, different sized cross plates 20, 22 can be used depending on whether spacers 18 are positioned between the first and second plates 14, 16.

Preferably, the cross plates 20, 22 are oriented perpendicular to the first and second plates 14, 16 (or, when present, the one or more spacers 18) so as to define the volume of the tissue slicing mold 12 as a cuboid.

The tissue slicer system 10 also includes a sliding stage 24 that is slidably coupled to the tissue slicer system 10. The sliding stage 24 allows a biological tissue specimen positioned in the tissue slicing mold 12 to be moved to a plurality of different slicing planes. In some embodiments, the sliding stage 24 can be a power-driven sliding stage. For instance, the sliding stage 24 can be coupled to a motor 32 that is configured to translate or otherwise move the sliding stage 24 through a plurality of different slicing planes. In some embodiments, the sliding stage 24 can be mechanically driven. As an example, the sliding stage 24 can be incremented through a plurality of different slicing planes using a suitable mechanism. One example of a suitable mechanism is a rack and pinion with a Geneva gear. An example of a sliding stage 24 including a rack 34 and pinion 36 is shown in FIG. 3. Another example of a suitable mechanism, as mentioned above, is a step motor or other motion device.

A slit 26 is disposed in the first and second plates 14, 16 and is configured to receive a blade for slicing a biological tissue specimen positioned in the tissue slicing mold 12. Preferably, the slit 26 is located approximately at the center of the tissue slicing mold 102. A similar slit 26 is also disposed in the one or more spacers 18. Each spacer 18 may thus include a single plate in which the slit 26 is disposed, or may be composed of two plates of similar thickness that can be positioned such that they are separated by a distance not less than that of the slit 26.

The slit 26 guides a thin, long blade 28, shown in FIG. 2, that minimizes the force applied to the biological tissue specimen compared to a thicker blade. By way of example, the blade 28 may be a commercially-available feather blade. Also shown in FIG. 2, the application of extraneous forces to the biological tissue specimen is reduced by the design of a modified blade holder 30. The blade holder 30 does not apply any forces to the tissue, unlike conventional designs that attach along the length of the blade 28. Instead, the blade holder 30, following a bow saw concept, attaches to the blade 28 only at its two ends at points that are outside of the tissue slicing mold 12. As a result of this design, the blade holder 30 does not exert force on the tissue specimen.

Together with the sliding stage 24, the slit 26 permits serial slicing of biological tissues, such as fresh, fatty tissue specimens, into uniformly thick slices. As an example, the tissue slicer system 10 is capable of slicing a biological tissue specimen to obtain tissue slices with a thickness on the order of 3 mm. The tissue specimen is encapsulated within a hydrogel in the tissue slicing mold 12 and tissue slicing can be performed without disturbing this tissue-hydrogel block.

The tissue slicer system 10 is preferably composed of a material that can be chilled to facilitate the fixation of a hydrogel. As an example, the tissue slicer system 10 can be composed of a metal, in whole or in part. For instance, the tissue slicer system 10 does not need to be composed of metal in its entirety; rather, the surfaces of the tissue slicer system 10 that will make contact with the hydrogel can be composed of a thermally conductive material, such as metal. By having thermally conductive material disposed on the surfaces of the tissue slicer system 10 that will contact the hydrogel, these contact surfaces can be pre-cooled to induce gelation of the hydrogel on contact. This gelation seals the internal volume of the sample being processed. The ability to chill the tissue slicer system 10 facilitates tissue slicing to be accomplished within the 1-hour guideline for cold ischemic time.

The features of the tissue slicer system 10 enable very thin slicing of challenging tissues (e.g., breast) within the 1-hour time limit that must be observed in order to work with surgical breast specimens, either in the clinic or in a research setting. Otherwise, large, fatty specimens would require a prolonged cooling time to compensate for the lack of support and/or additional forces. It has been discovered that for breast tissues comparable to a large lumpectomy in size, the tissue slicer system 10 and its tissue slicing mold 12, permits slicing of large biological tissue specimens within one hour of resection. Typically, this task requires 3-4 hours to complete using a rotary slicer.

Having described an example of the tissue slicer system 10 of the present invention, an example of a method for its use is now provided. The tissue slicer is initially kept in a freezer, and then placed on cold plate while the biological tissue specimen is being prepared. This active cooling accelerates stabilization of flaccid specimens (e.g., for lumpectomies) as required for thin slicing. Slicing is constrained to occur within one hour of resection to conform to guidelines for cold ischemic time for breast specimens set by the College of American Pathologists/American College of Surgical Oncologists.

The size of the tissue slicer is then adjusted to an appropriate size for the biological tissue specimen. By way of example, one or more spacers, or no spacers at all, are selected for the desired internal width of the tissue slicing mold. The appropriately sized cross plates are then also selected. The spacers, if any are used, and the cross plates are positioned in the tissue slicer and then the distance between the cross plates is adjusted to accommodate the biological tissue specimen.

A hydrogel is used to stabilize the biological tissue specimen and to provide support along with the tissue slicing mold for slicing. Preferably, a rapid-setting hydrogel is used to facilitate the completion of the tissue slicing procedure within the desired window of time, which for some tissues may be one hour. The biological tissue specimen is then embedded into the hydrogel and the entire slicer is placed in refrigeration to accelerate tissue cooling, thereby improving the quality of slicing for tissues that lack internal support, such as flaccid breast tissues. An alternative method is to initially place the tissue specimen into a pre-cooled cuboid mold having a size that matches the tissue slicer system, and then to surround the specimen with hydrogel. The entire block is then cooled until the hydrogel is stiffened, and then the specimen is transferred to the tissue slicer system.

After the hydrogel has set and an optimal temperature of the biological tissue specimen is achieved, the tissue slicer is removed from refrigeration. The hydrogel is then loosened from the interior of the tissue slicing mold to facilitate adjusting the biological tissue specimen into different slicing planes. The blade slot of the tissue slicer is then aligned with the appropriate location for the first slice. Optionally, the first slice can be made to remove excess hydrogel before encountering tissue.

Slicing through the first slice containing the biological tissue specimen then commences. Slices are typically made from the medial aspect to the lateral aspect of the specimen (or lateral-to-medial, depending on the laterality of the breast from which the specimen was resected). In this manner, each slice contains an entire cross-section of the whole specimen demonstrating anterior, posterior, superior, and inferior margins simultaneously.

After a slice is made, the blade is uncoupled from the blade handle, such as by releasing the blade from the blade handle, and the handle is then removed from the blade. The blade can then be removed from the tissue slicer by horizontally pulling the blade from the tissue slicer. This approach reduces strain on the tissue and, thus, reduces the risk of tearing the tissue that could be caused by otherwise dragging the blade against delicate structures in the exposed, cut surface, such as may occur by vertically removing the blade. In some configurations, sufficient space is allowed surrounding the tissue slicer such that the blade can be extracted without pulling on the tissue. For instance, when the tissue slicer includes a power-driven sliding stage, a sufficiently sized gap can be provided in the power-driven stage that allows for the blade to pass through the tissue and to be extracted without pulling on the tissue.

The blade is then recoupled to the blade holder and the tissue slicing mold is moved into alignment with the next slicing plane. Optionally, the spacers can be removed when adjusting the tissue slicing mold. A ruler can be disposed on one of the plates defining the tissue slicer to facilitate accurate identification of slicing planes.

Slicing is repeated in this manner until the entire biological tissue specimen is cut into a series of slices with the desired thickness. As an example, the slice thickness may be four millimeters, which can expedite adequate fixation, which occurs diffusively, as well as tissue processing for larger, whole-mount sections. This thickness, which cannot he achieved for breast tissues utilizing freehand slicing of the unfixed specimen, also maximizes the surface area that is exposed, visible, and palpable for conventional sampling of areas that best represent the tumor.

When slicing is completed, one of the cross plates is removed and the initially cut excess hydrogel, if any, is removed. Each tissue slice is then placed on a porous divider for placement in fixative on a custom rack. In some embodiments, the porous divider can be composed of fiber reinforced plastic ("FRP"), which may be reinforced with fiberglass, or the porous divider may be composed of a semipermeable material with sufficient residual strength to support the tissue when saturated. In general, the divider is configured to maintain the flat shape of the tissue slice and does not allow for the tissue slice to curl. Once all of the slices have been prepared and the cross plate is removed, the following procedure is generally used to remove the slices. A divider is held against the first slice, which is separated from the others and gently pushed onto the divider. The divider is labeled and placed onto a shelf in the fixing rack and the process of removing the slices onto a divider is repeated for all the remaining slices.

The slices can then be placed in formalin bath for overnight fixation. The following day, the fixed tissue slices are processed for whole-mount sections, or sampled using conventional techniques (e.g., excision of sparsely-sampled, small tissue selections deemed grossly to be representative of tumor, and processing of these samples).

Alternatively, small section sub-sampling can be performed on the fresh, unfixed tissue slices to provide tissue for immediate analysis, such as cryotomy. This latter approach offers several workflow efficiencies in the pathology laboratory (i.e., a fume hood is not required for sampling; two-step process done at once). This sampling is currently not possible without achieving very thin tissue slices, such as can be achieved using the tissue slicer of the present invention.

The present invention has been described in terms of one or more preferred embodiments, and it should be appreciated that many equivalents, alternatives, variations, and modifications, aside from those expressly stated, are possible and within the scope of the invention.

The invention claimed is:

1. A tissue slicer system for slicing a biological tissue specimen into a plurality of substantially uniformly thick slices, comprising:
    a tissue slicing mold configured to receive a biological tissue specimen, the tissue slicing mold comprising:
      a first plate;
      a second plate opposing the first plate;
      a first cross plate removably positioned between and generally perpendicular to the first plate and the second plate;
      a second cross plate opposing the first cross plate and removably positioned between and generally perpendicular to the first plate and the second plate;
      a slit disposed in the first plate and the second plate, the slit defining a guide for a blade; and
    a sliding stage coupled to the tissue slicing mold, wherein the sliding stage is slidably adjustable relative to the slit so as to align the tissue slicing mold with a plurality of different slicing planes.

2. The tissue slicer system as recited in claim 1, further comprising at least one spacer capable of being removably positioned parallel to the first plate and between the first plate and edges of the first and second cross plates that face the first plate.

3. The tissue slicer system as recited in claim 2, wherein an internal volume of the tissue slicing mold is adjustable by adjusting a separation between the first and second cross plates and by positioning the at least one spacer between the first plate and the edges of the first and second cross plates that face the first plate.

4. The tissue slicer system as recited in claim 2, wherein the at least one spacer comprises two plates that are separated by a distance not less than a width of the slit.

5. The tissue slicer system as recited in claim 2, wherein the at least one spacer has disposed therein a slit that defines a guide for a blade.

6. The tissue slicer system as recited in claim 1, further comprising:
    a blade extending from one end to a second end and capable of being moved through the slit to slice a biological tissue specimen positioned in the tissue slicing mold; and
    a blade holder coupled to the first end and the second end of the blade without coupling along a length of the blade.

7. The tissue slicer system as recited in claim 1, wherein an internal volume of the tissue slicing mold is adjustable by adjusting a separation between the first and second cross plates.

8. The tissue slicer system as recited in claim 1, wherein the tissue slicing mold is configured to receive a biological tissue specimen embedded in a hydrogel.

9. The tissue slicer system as recited in claim 1, wherein the first plate and the second plate are parallel to each other.

10. The tissue slicer system as recited in claim 1, wherein the first cross plate and the second cross plate are configured to be parallel to each other when positioned between and coupled to the first plate and the second plate.

11. The tissue slicer system as recited in claim 1, wherein the sliding stage is a mechanically-driven sliding stage.

12. The tissue slicer system as recited in claim 11, further comprising a motor coupled to the mechanically-driven sliding stage and configured to slidably adjust the mechanically-driven sliding stage relative to the slit so as to align the tissue slicing mold with a plurality of different slicing planes.

13. The tissue slicer system as recited in claim 11, wherein the mechanically-driven sliding stage includes a rack and pinion configured to slidably adjust the mechanically-driven sliding stage relative to the slit so as to align the tissue slicing mold with a plurality of different slicing planes.

14. The tissue slicer system as recited in claim 1, wherein the tissue slicing mold further includes a bottom plate perpendicular to the first and second plates and to the first and second cross plates, the bottom plate being configured to receive and support a biological tissue specimen.

15. The tissue slicer system as recited in claim 14, further comprising:
   a blade extending from one end to a second end and capable of being moved through the slit to slice a biological tissue specimen positioned in the tissue slicing mold; and
   a blade holder configured to couple to the first end and the second end of the blade without coupling along a length of the blade.

16. The tissue slicer system as recited in claim 15, further comprising a groove arranged in the bottom plate and configured to receive the blade after the blade slices through a biological tissue specimen supported on the bottom plate, such that the blade can be extracted from the tissue slicing mold without further contact with the biological tissue specimen.

* * * * *